United States Patent [19]

Arimura et al.

[11] Patent Number: 4,555,401
[45] Date of Patent: Nov. 26, 1985

[54] LIVE MUMPS VACCINE AND METHOD OF STABILIZING THE SAME

[75] Inventors: Hirofumi Arimura, Toyonaka; Yahiro Uemura, Hirakata; Yoshiomi Okuno, Ibaraki, all of Japan

[73] Assignee: The Green Cross Corporation, Osaka, Japan

[21] Appl. No.: 589,863

[22] Filed: Mar. 19, 1984

Related U.S. Application Data

[63] Continuation of Ser. No. 351,401, Feb. 23, 1982, abandoned.

[30] Foreign Application Priority Data

Jul. 3, 1980 [JP] Japan .................................. 55-90943

[51] Int. Cl.⁴ ............................................ A61K 39/165
[52] U.S. Cl. ...................................................... 424/89
[58] Field of Search ............................................ 424/89

[56] References Cited

U.S. PATENT DOCUMENTS

| | | | |
|---|---|---|---|
| 3,555,149 | 1/1971 | Buynak et al. | 424/89 |
| 4,072,565 | 2/1978 | Weiss et al. | 424/89 |
| 4,147,772 | 4/1979 | McAleer et al. | 424/89 |
| 4,337,242 | 6/1982 | Markus et al. | 424/89 |
| 4,338,335 | 7/1982 | McAleer et al. | 424/89 |

FOREIGN PATENT DOCUMENTS

| | | | |
|---|---|---|---|
| 0028563 | 5/1981 | European Pat. Off. | 424/89 |
| 0065905 | 12/1982 | European Pat. Off. | 424/89 |
| 2215946 | 8/1974 | Fed. Rep. of Germany | 424/89 |
| 2076787 | 10/1971 | France | 424/89 |
| 1049386 | 11/1966 | United Kingdom | 424/89 |
| 1575155 | 9/1980 | United Kingdom | 424/89 |

OTHER PUBLICATIONS

Smorodintsev et al., *Acta Virol.*, 9: 240–247, (1965).
Yamanishi et al., *Biken Journal*, vol. 16, 161–166, (1973).
Physician's Desk Reference for 1983, pp. 1324–1325.

*Primary Examiner*—Shep K. Rose
*Attorney, Agent, or Firm*—Cushman, Darby & Cushman

[57] ABSTRACT

A live mumps vaccine can be stabilized to a great extent by adding in an amount, effective for stabilizing said vaccine, at least one stabilizer selected from the group consisting of albumin and gelatin.

6 Claims, No Drawings

LIVE MUMPS VACCINE AND METHOD OF STABILIZING THE SAME

CROSS REFERENCE TO RELATED APPLICATION

This application is continuation of our earlier application Ser. No. 351,401, filed Feb. 23, 1982, now abandoned.

This invention relates to a preparation of live mumps vaccine, and more particularly to a live mumps vaccine preparation characterized by adding in an amount, effective for stabilizing a live mumps vaccine preparation, albumin and/or gelatin to the live mumps vaccine preparation.

Mumps vaccine is produced by inactivating mumps virus or by weakening its toxicity. Mumps virus is known as a virus causing epidemic parotitis. After this virus was discovered by Johnson et al. in 1934, its cultivation has become possible by the use of grown hen's egg, yolk sac, amniotic cavity or the like, and inactivated mumps vaccine and live mumps vaccine (hereinafter, referred to as "LMV") have been produced therefrom. Today, LMV scarcely causing subsidiary ill effects and having a high titer is available, so that inactivated mumps vaccine has almost lost its practical meanings. Though LMV was originally developed and used as a vaccine for controlling mumps virus, the value of LMV as a medical drug is attracting much increasing interests currently, since its anticarcinogenic action was clinically demonstrated lately in addition to its original role.

With the aim of improving the stability of LMV preparation which has acquired such a very great usefulness, the present inventors have conducted elaborated studies on the stabilization of this product which has hitherto been provided in the form of a liquid product, as well as on the stabilization of this product at the time of freeze-drying treatment and on the stabilization of dry sample in the lapse of time. As the result, it has been found that LMV becomes remarkably stable by coexistence of albumin, gelatin or their mixture not only in aqueous medium but also in the state of dried solid. This invention was accomplished based on this finding.

Thus, according to this invention, there is provided an LMV composition comprising LMV and a stabilizing amount of at least one stabilizer selected from albumin and gelatin.

The LMV composition of this invention may be an aqueous suspension of LMV or a powdery solid. They may contain adjuvants preferably usable in the application to human body. In preparing a solid composition from said aqueous suspension, the decrease in activity of LMV can be prevented by employing the technique of freeze-drying.

As the albumin used in this invention, human albumin is preferable in point of antigenicity. However, the albumin is not limited to human albumin, but wide variety of commercially available albumins which can be administered to human body for the purpose of medical treatment may be used without restriction. As the gelatin, any gelatin may be used without restriction so far as it is usable for medical treatment. More preferably, said gelatin is that having a uniform component.

The LMV of this invention is not critical, but it may be any LMV so far as its toxicity is weakened according to the widely known process for the production of LMV and it is purified to an extent enabling its use in medical treatment. In this specification, the LMV derived from Urabe strain offered by Biseibutus Kenkyujo, Osaka Daigaku (Research Institute of Microorganisms, Osaka University) will be mentioned.

A larger amount of the stabilizer, such as albumin, gelatin or the like, added gives a greater effect of stabilization, though the effect may also be dependent on the amount of LMV in the preparation. When the stabilizer is added into an aqueous medium, the final concentration of stabilizer should be 1–10% W/V. When it is added to a powder, its final concentration should be 5–20% W/W. When albumin and gelatin are used in combination in an aqueous medium, their individual final concentration should be 0.1–5% W/V and their total final concentration should be 1–10% W/V. When they are used in combination in a powder, their individual final concentration should be 1–10% W/W and their total final concentration should be 5–20% W/W.

Hereunder, this invention will be explained in more detail with reference to experimental examples and examples. The p.f.u. (plaque forming unit; LMV titer) used in the experimental examples have been determined according to the description of "Virus Jikkengaku (Experimental Virology)", edited by Gakuyukai of Kokuritsu Yobo Eisei Kenkyujo (The National Institute of Health, Japan) and published by Maruzen (1967).

Experimental Example 1: Stabilizing Effect on Aqueous Medium Containing LMV

Various stabilizers were added to $6.5 \times 10^5$ p.f.u./ml (0.9% aqueous solution of sodium chloride) each of LMV suspensions. The mixtures thus obtained were tested on stability by allowing them to stand in a thermostatted water bath kept at 20° C. The results are shown in Table 1.

TABLE 1

|  | Stabilizer | Final concentration, % (W/V) | Residual titer after one month at 20° C. (%) |
|---|---|---|---|
| This invention | Albumin | 1 | 40 |
|  | " | 9 | 50 |
|  | Gelatin | 2 | 43 |
|  | " | 8 | 59 |
|  | Albumin + Gelatin | 0.1 + 2 | 49 |
|  | " | 0.5 + 1 | 42 |
|  | " | 1.0 + 1 | 46 |
|  | " | 2.0 + 0.1 | 52 |
|  | " | 5.0 + 0.1 | 62 |
| Control | None |  | <1 |

Experimental Example 2: Stabilizing Effect on Freeze-dried Product of LMV

Various stabilizers were mixed into a freeze-dried product of LMV having a total activity of $1.8 \times 10^5$ p.f.u. The mixtures were tested on stability by allowing them to stand at −10° C. for one month. The results are shown in Table 2.

TABLE 2

|  | Stabilizer | Concentration in dry product, % (W/W) | Residual titer (%) |
|---|---|---|---|
| This invention | Albumin | 5 | 84 |
|  | " | 10 | 93 |
|  | Gelatin | 5 | 83 |

TABLE 2-continued

| Stabilizer | Concentration in dry product, % (W/W) | Residual titer (%) |
|---|---|---|
| " | 10 | 96 |
| Albumin + Gelatin | 1 + 1 | 84 |
| " | 1 + 10 | 96 |
| " | 1 + 15 | 97 |
| " | 10 + 1 | 96 |
| " | 5 + 10 | 95 |
| " | 8 + 8 | 97 |
| Control   None | | <10 |

EXAMPLE 1

LMV was diluted to a titer of $2 \times 10^5$ p.f.u./ml with physiological sodium chloride solution (100 ml), to which were added 5% W/V of albumin and 0.5% W/V of gelatin. The resulting mixture was sterilized and filtered. The filtrate was poured dividingly and then freeeze-dried. The freeeze-dried LMV thus obtained had a titer of $6.9 \times 10^5$ p.f.u./mg. It retained an activity of $6.8 \times 10^8$ p.f.u./mg even after being stored at $-10°$ C. for one month.

EXAMPLE 2

A freeze-dried LMV was prepared by repeating the procedure of Example 1, except that the 5% W/V of albumin and 0.5% W/V of gelatin used in Example 1 was replaced with 8% W/V of albumin.

What is claimed is:

1. A stable live mumps vaccine composition comprising a live mumps vaccine and a stabilizing amount of a stabilizer consisting of albumin and gelatin.

2. A live mumps vaccine composition according to claim 1, wherein said composition is an aqueous fluid.

3. A live mumps vaccine composition according to claim 2, wherein the amount of said stabilizer is 1–10% W/V.

4. A live mumps vaccine composition according to claim 1, wherein said composition is a solid.

5. A live mumps vaccine composition according to claim 4, wherein the amount of said stabilizer is 5–20% W/W.

6. A mthod for stabilizing live mumps vaccine which comprises contacting a live mumps vaccine with a mixture consisting of albumin and gelatin as a stabilizer.

* * * * *